(12) United States Patent
Barker, Jr. et al.

(10) Patent No.: US 6,440,660 B1
(45) Date of Patent: *Aug. 27, 2002

(54) OLIGONUCLEOTIDE MEDIATED REVERSAL OF DRUG RESISTANCE

(75) Inventors: Robert H. Barker, Jr., Canton, MA (US); Eliezer Rapaport, Belmont, MA (US); Paul C. Zamecnik, Shrewsbury, MA (US)

(73) Assignees: Hybridon, Inc., Cambridge, MA (US); Worchester Foundation for Biomedical Research, Shrewsbury, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/745,485

(22) Filed: Nov. 12, 1996

Related U.S. Application Data

(62) Division of application No. 08/634,588, filed on Apr. 18, 1996, which is a continuation of application No. 08/560,474, filed on Nov. 17, 1995, now abandoned.

(51) Int. Cl.$^7$ .......................... C12Q 1/68; C07H 21/04; C12N 15/85
(52) U.S. Cl. .......................... 435/6; 435/91.1; 435/325; 435/375; 536/23.1; 536/24.5
(58) Field of Search .................. 514/44; 435/6, 435/91.1, 325; 536/23.1, 24.5

(56) References Cited

U.S. PATENT DOCUMENTS 5,585,479 A * 12/1996 Hoke et al. ................. 536/24.5

FOREIGN PATENT DOCUMENTS

| WO | WO 90/00624 | 1/1990 |
| WO | WO 94/02498 | 2/1994 |

OTHER PUBLICATIONS

Milligan et al., Current concepts in antisense drug design, J. of Med. Chem., v.36 (14), pp. 1923–1937, Jul. 1993.*
Foote et al., Amplification of the multidrug resistance gene in some chloroquine resistant isolates of P. falciparum, Cell, v. 57, pp. 921–930, Jun. 1989.*
Rapaport et al., Antimalarial activities of oligodeoxynucleotide phosphorothioates in chloroquine resistant Plasmodium falciparum, Proc. Natl. Acad. Sci., v. 89, pp. 8577–8580, Sep. 1992.*
Clark et al., Non–sequence specific antimalarial activity of oligodeoxynucleotides, Mol. and Biochem. Parasit., v. 63, pp. 129–134, 1994.*
Triglia et al., Amplification of the multidrug resistance gene pfmdr1 in Plasmodium falciparum has arisen as multiple independent events, Mol. Cell. Biol., v. 11, pp. 5244–5250, 1991.*
Wilson et al., Amplification of pfmdr1 associated with mefloquine and halofantrine resistance in Plasmodium falciparum from Thailand, Mol. and Biochem Parasit., vo. 57, pp. 151–160, 1993.*
Cowman, A.F., The P–glycoprotein homologues of Plasmodium falciparum: Are they involved in chloroquine resistance?, Parasitology Today, v. 7 (4), pp. 70–76, 1991.*
Zalis et al., Characterization of the pfmdr2 gene for Plasmodium falciparum, Mol. and Biochem. Parasit., v. 62, pp. 83–92, 1993.*
Gewirtz et al., Facilitating oligonucleotide delivery: Helping antisense deliver on its promise, Proc. Natl. Acad. Sci., vol. 93, pp. 3161–3163, Apr. 1996.*
Rapaport et al. (1992) Proc. Natl. Acad. Sci. USA 89:8577–8580.
Tao et al. (1995) Antisense Res. Dev. 5:123–129.
Foote et al. (1989) Cell 57:921–930.
Wilson et al. (1989) Science 244:1184–1186.
Endicott et al. (1989) Ann. Rev. Biochem. 58:137–171.
Volkman et al. (1993) Mol. Biochem. Parasitol. 57:203–212.
Oduola et al. (1988) Exp. Parasitol. 67:354–360.
Peel et al. (1994) Am. J. Trop. Med. Hyg. 51:648–658.
Wilson et al. (1993) Mol. Biochem. Parasitol. 57:151–160.
Barker et al. (1996) Proc. Natl. Acad. Sci. USA 93:514–518.
Macomber et al. (1966) Science 152:1374–1375.
Valecha et al. (1992) Ind. J. Malariol. 29:47–53.
Miki et al. (1992) Exp. Parasitol. 72:134–142.
Sartorius et al. (1991) Nucleic Acids Research 19:1613–1618.
Vespieren et al. (1990) Nucleic Acids Research 18:4711–4717.
Bzik et al. (1987) Proc. Natl. Acad. Sci. USA 84;8360–8364.
Sartorius et al. (1991) Parasitiology Today 7:90–93.
Milligan et al. (1993) J. of Med. Chem. 36:1923–1937.
Clark et al. (1994) Mol. and Biochem Parasit. 63:129–134.
Triglia et al. (1991) Mol. Cell. Biol. 11:5244–5250.
Cowman (1991) Parasitology Today 7:70–76.
Zalis et al. (1993) Mol. and Biochem. Parasit. 62:83–92.
Stull et al. (1995) Pharmaceutical Research 42:465–481.

* cited by examiner

Primary Examiner—Andrew Wang
(74) Attorney, Agent, or Firm—Hale & Dorr LLP

(57) ABSTRACT

The present invention provides methods of resensitizing an anti-drug-resistant infectious agent to a drug. Also disclosed are synthetic oligonucleotides having a nucleotide sequence complementary to a region of pfmdr1 nucleic acid, and methods of down-regulating the expression of pfmdr nucleic acid using such oligonucleotides.

16 Claims, 9 Drawing Sheets

OLIGONUCLEOTIDE MEDIATED REVERSAL OF DRUG RESISTANCE

CROSS-REFERENCE TO RELATED APPLICATIONS

This application is a continuation-in-part of copending patent application Ser. No. 08/634,588, filed Apr. 18, 1996, which is a continuation of patent application Ser. No. 08/560,474 entitled "OLIGONUCLEOTIDE MEDIATED REVERSAL OF DRUG RESISTANCE", filed Nov. 17, 1995 now abn.

FIELD OF THE INVENTION

The present invention relates to drug resistance among infectious organisms or agents. More particularly, this invention relates to the use of antisense oligonucleotides to reverse such drug resistance, thereby resensitizing the infectious agents to therapeutic drugs.

BACKGROUND OF THE INVENTION

A number of diseases are caused by infectious organisms which have become resistant to various chemotherapeutic drugs commonly used to treat such organisms. One such disease is malaria. Malaria is estimated to afflict more than 200 million people annually (WHO (1992) Bull. W.H.O. 70:801–804). While presently confined primarily to the tropics where it is endemic, malaria was formerly very wide spread, including the United States. However, in the late 1980's small foci of periodic transmission of malaria in San Diego County were reported (Anonymous (1990) JAMA 263:1617), demonstrating that transmission capacity is still present in the United States, and that under the right circumstances, malaria could possibly become endemic once again.

Malaria is caused by infection with one or more species of Plasmodium. Three species (P. vivax, P. ovale, and P. malariae) produce relatively mild symptoms consisting of spiking periodic fever, anemia, and some jaundice. In contrast, infection with P. falciparum can lead to coma and death unless chemotherapy is initiated, and is responsible for about 800,000 deaths per year among African children under 5 years (WHO (1992) Bull. W.H.O. 70:801–804; and WHO (1992) WHO Weekly Epidemiological Record 22: p. 161–167).

Malaria infection is transmitted via the bite of an infected Anopheline mosquito during her blood meal. The sporozoite stage of the parasite is injected into the human host in mosquito saliva, and sporozoites then migrate to the liver where they invade hepatocytes, becoming intracellular parasites. Multiplication occurs within hepatocytes, which then rupture to release merozoite-stage parasites. These in turn invade circulating erythrocytes, beginning the asexual erythrocytic cycle of the parasite life cycle. It is the erythrocytic stages which are responsible for pathology to the human host. Within the erythrocyte, merozoites first develop into ring stage parasites, then trophozoites, then schizonts. Parasite DNA replication occurs during the trophozoite stage, giving rise to 16–20 merozoites at the end of schizogony. Mature schizonts cause the host erythrocyte to lyse, releasing merozoites which then reinvade erythrocytes to continue the cycle.

A small proportion of merozoites develop into male or female gametocytes. When drawn into a mosquito midgut during her blood meal, these erupt from the erythrocytes, fertilization occurs, and the zygotes penetrate the mosquito midgut wall to become oocysts. After asexual multiplication within oocysts, sporozoites are released, which migrate to the insect salivary glands to await the next mosquito blood meal. Injection of sporozoites in mosquito saliva during that next meal reinitiates the parasite life cycle.

Malaria has been treated with a variety of drugs, including anti-folate compounds such as pyrimethamine, trimethoprim, and proguanil (which inhibit the enzyme dihydrofolate reductase (Bzik et al. (1987) Proc. Natl. Acad. Sci. USA 84:8360–8364)), sulfonamides, (which inhibit dihydropteroate synthetase (Brooks et al. (1994) Eur. J. Biochem. 224:397–405), 4-aminoquinolines such as chloroquine (quinine analogs), sulfones, sulfanamides, and tetracyclines.

The antifolate drugs work by binding their target enzymes, thereby preventing normal enzyme function. While effective, resistance to these drugs can be mediated by selection for one or at most two point mutations which prevent binding of the drug to the active site (Brooks et al. (1994) Eur. J. Biochem. 224:397–405; Basco et al. (1995) Mol. Biochem. Parricidal. 69:135–138). Consequently, resistance to these drugs appeared fairly soon after these drugs were introduced (Peters, Chemotherapy and Drug Resistance in Malaria. (1987) London: Academic Press, pp. 15–20).

Until recently, chloroquine was by far the most commonly used antimalarial compound, owing to its low cost and lack of side effects compared with the antifolates (Peters, Chemotherapy and Drug Resistance in Malaria. (1987) London: Academic Press, pp. 5–14). However, after years of widespread chloroquine use, foci of resistant P. falciparum have been identified wherever malaria is endemic. Because of this widespread resistance, first antifolates, and now mefloquine have largely replaced chloroquine for treatment of P. falciparum and P. vivax as well (Peters, Chemotherapy and Drug Resistance in Malaria. (1987) London: Academic Press, pp. 659–670).

Mefloquine (a quinalone-methanol) has been shown to be effective against multi-drug resistant strains of P. falciparum (Harinasuta et al. (1983) Bull. WHO 61:299–305), and also been used for prophylactic use by travellers (Anonymous (1990) JAMA 263:2729–2737). While somewhat expensive and not without side effects, it remains the drug of choice for treating multi-drug resistant malaria (White (1988) Eur. J. Clin. Pharmacol. 34:1–14; and Anonymous (1990) JAMA 263:2729–2737). However, despite extensive measures to protect the efficacy of mefloquine, resistance has developed rapidly, and has even been found in areas where the drug has not been used clinically. In addition, wide spread cross resistance to other drugs has been demonstrated including structurally unrelated compounds such as halofantrine (Ringwald et al. (1990) Lancet 335:421–422; Gay et al. (1990) Lancet 336:1262; and Wilson et al. (1993) Mol. Biochem. Parricidal. 57:151–160), and artemesinin (Wilson et al. (1993) Mol. Biochem. Parricidal. 57:151–160), in addition to quinine (Brasseur et al. (1992) Am. J. Trop. Med. Hyg. 46:1–7; Brasseur et al. (1992) Am. J. Trop. Med. Hyg. 46:8–14; and Suebsaeng et al. (1986) Bull. WHO 64:759–765). The apparent cross-resistance to quinine is particularly significant because intravenous quinine remains the treatment of last recourse in cases of severe or cerebral malaria (Warrell et al. (1990) Trans. R. Soc. Trop. Med. Hyg. 84(suppl 2):1–65).

There is thus a need for improved chemotherapeutic drugs whose use inhibits or controls parasite infection without ultimately resulting in widespread resistance to such drugs and to those related thereto.

New chemotherapeutic agents have been developed which are capable of modulating cellular and foreign gene expression (see, Zamecnik et al. (1978) *Proc. Natl. Acad. Sci.* (USA) 75:280–284). These agents, called antisense oligonucleotides, bind to target single-stranded nucleic acid molecules according to the Watson-Crick rule or by other modes of hydrogen bonding, as well as base stacking, or to double stranded nucleic acids by the Hoogsteen rule of base pairing, or to and in doing so, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Antisense oligonucleotides have been developed as antiparasitic agents, although none have been demonstrated to reverse drug resistant phenotype of a drug resistant parasite strain. PCT publication No. WO 93/13740 discloses the use of antisense oligonucleotides directed to nucleic acids encoding the dihydrofolate reductase-thymidylate synthase gene of *P. falciparum* to inhibit propagation of drug-resistant malarial parasites. Rapaport et al. (*Proc. Natl. Acad. Sci. (USA)* (1992) 89:8577–8580) teaches inhibition of the growth of chloroquine-resistant and chloroquine-sensitive *P. falciparum* in vitro using oligonucleotides directed to the dihydrofolate reductase-thymidylate synthase gene. PCT publication No. WO 94/12643 discloses antisense oligonucleotides directed to nucleic acids encoding a carbamoyl phosphate synthetase of *P. falciparum*. Tao et al. (*Antisense Res. Dev.* (1995) 5:123–129) teaches the uptake of antisense oligonucleotides by a schistosome parasite.

However, a need still remains for the development of oligonucleotides that are capable of inhibiting the replication of parasites and other infectious organisms. There is also a need for oligonucleotides which have the ability to reverse a drug resistant phenotype of a drug-resistant infectious organism, thereby resensitizing the organism to a therapeutic drug.

SUMMARY OF THE INVENTION

It is known that drug resistance among some infectious agents is mediated by enhanced expression of genes which actively subvert the activity of the relevant drugs, either by facilitating extracellular export of the drug (in the case of mdr-like genes), or by actively destroying the drug. It has been discovered that oligonucleotides specific for the pfmdr1 gene in the presence of mefloquine can reverse the drug-resistant phenotype of a mefloquine-resistant strain of parasite, thereby increasing parasite sensitivity to mefloquine. This discovery has important clinical consequences in facilitating continued use of mefloquine treatment in afflicted geographical areas where otherwise, mefloquine use is becoming increasingly restricted, due to decreased efficacy.

The discovery has been exploited to develop the present invention, which includes oligonucleotides, methods, and pharmaceutical formulations useful for reversing drug resistance and increasing parasite sensitivity to various chemotherapeutic drugs such as mefloquine, for inhibiting the expression of the pfmdr1 gene, and for treating diseases resulting from the infectious agent, such as malaria. The present invention represent a significant departure from previous applications of the antisense technology which have focused on the use of antisense oligonucleotides to directly inhibit growth and replication of infectious organisms.

In a first aspect, the invention provides a synthetic oligonucleotide having a nucleotide sequence complementary to a pfmdr1 nucleic acid. In one embodiment, the oligonucleotide of the invention is complementary to a region of pfmdr1 nucleic acid selected from the group consisting of a conserved region, an ATP binding site, a translational start site, and a *Plasmodium falciparum*-specific region.

As used herein, the term "synthetic oligonucleotide" includes chemically synthesized polymers of about five and up to about 50, preferably from about 19 to about 30 ribonucleotide and/or deoxyribonucleotide monomers connected together or linked by at least one, and preferably more than one, 5' to 3' internucleotide linkage.

For purposes of the invention, the term "oligonucleotide sequence that is complementary to" a nucleic acid is intended to mean an oligonucleotide that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means, including other forms of hydrogen bonding, base stacking, or in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

The term "region," as used herein, refers to contiguous nucleotides making up a particular site, such as the translational start site or ATP binding cassette, as well as up to 20 nucleotides upstream and/or downstream from the site, or surrounding and including the site. The term "conserved" refers to nucleotide sequences within the gene of a species that are also found in other related or unrelated species or even genera. A "*Plasmodium falciparum*-specific region" encompasses nucleotide sequences which are not found in other species.

In some embodiments the oligonucleotide of the invention has a nucleic acid sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

The oligonucleotides of the invention are modified in some embodiments. Preferred embodiments include at least one non-phosphodiester internucleotide linkage selected from the group consisting of phosphorothioates, phosphorodithioates, alkylphosphonates, alkylphosphonothioates, phosphoramidates, carbamates, acetamidates, carboxymethyl esters, carbonates, phosphate triesters, and combinations thereof in the case where more than one modified linkage is present. Particularly preferred embodiments have phosphorothioate internucleotide linkages. Some oligonucleotides of the invention include at least one ribonucleotide, at least one deoxyribonucleotide, or both. One preferred embodiment includes at least one 2'-O-alkylribonucleotide.

In another aspect, the invention provides a method of resensitizing an anti-malarial drug-resistant Plasmodium parasite to an anti-malarial drug, thereby reversing its drug-resistant phenotype. In this method, the parasite is cultured in the presence of a synthetic oligonucleotide complementary to a pfmdr-specific nucleic acid for a time sufficient to enable the oligonucleotide to hybridize to the nucleic acid. The parasite is then contacted and cultured with an anti-malarial drug in the presence of the oligonucleotide. In this way, the drug-resistant phenotype of the parasite can be reversed such that it can now be controlled by the drug. In preferred embodiments, the oligonucleotide used in the method of the invention are specific for a conserved region, an ATP binding site, a translational start site, or a *Plasmo-*

*dium falciparum*-specific region of pfmdr1 nucleic acid, as described above. Anti-malarial drugs used in some embodiments are mefloquine, quinine, chloroquine, and/or derivatives thereof. In some preferred methods, mefloquine is used.

In another aspect, the invention provides a method of down-regulating the expression of pfmdr nucleic acid. In this method, the pfmdr nucleic acid is contacted with a synthetic oligonucleotide of the invention.

The invention also provides, in yet another aspect, a method of resensitizing a drug-resistant infectious organism to an anti-infectious organism drug, thereby reversing the drug-resistant phenotype of the organism. In this method, the infectious organism is cultured in the presence of a synthetic oligonucleotide complementary to a nucleic acid required for the drug-resistant phenotype for a time sufficient to enable the oligonucleotide to hybridize to the nucleic acid. In some embodiments, the oligonucleotide is complementary to pfmdr1 nucleic acid. The infectious organism is then contacted and further cultured with an anti-infectious organism drug in the presence of the oligonucleotide. In some embodiments, the infectious organism is a Plasmodium parasite, the oligonucleotide is complementary to pfmdr1 nucleic acid, and the drug is chloroquine, mefloquine, or quinine.

The pfmdr1-specific oligonucleotides of the invention are also useful for examining the function of the pfmdr1 gene in a control parasite and in a drug resistant parasite. Presently, gene function can only be examined by the arduous task of making a "knock out" animal. This task is difficult, time-consuming and cannot be accomplished for genes essential to animal development, since the "knock out" would produce a lethal phenotype. To date it has not been possible to increase or decrease gene copy number of pfmdr1 in malaria using gene transcription experiments. Thus, a direct demonstration of the function of the pfmdr1 gene in mefloquine resistance has not been shown. The present invention overcomes the shortcomings of this model.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE PREFERRED EMBODIMENTS

Figure 1A:
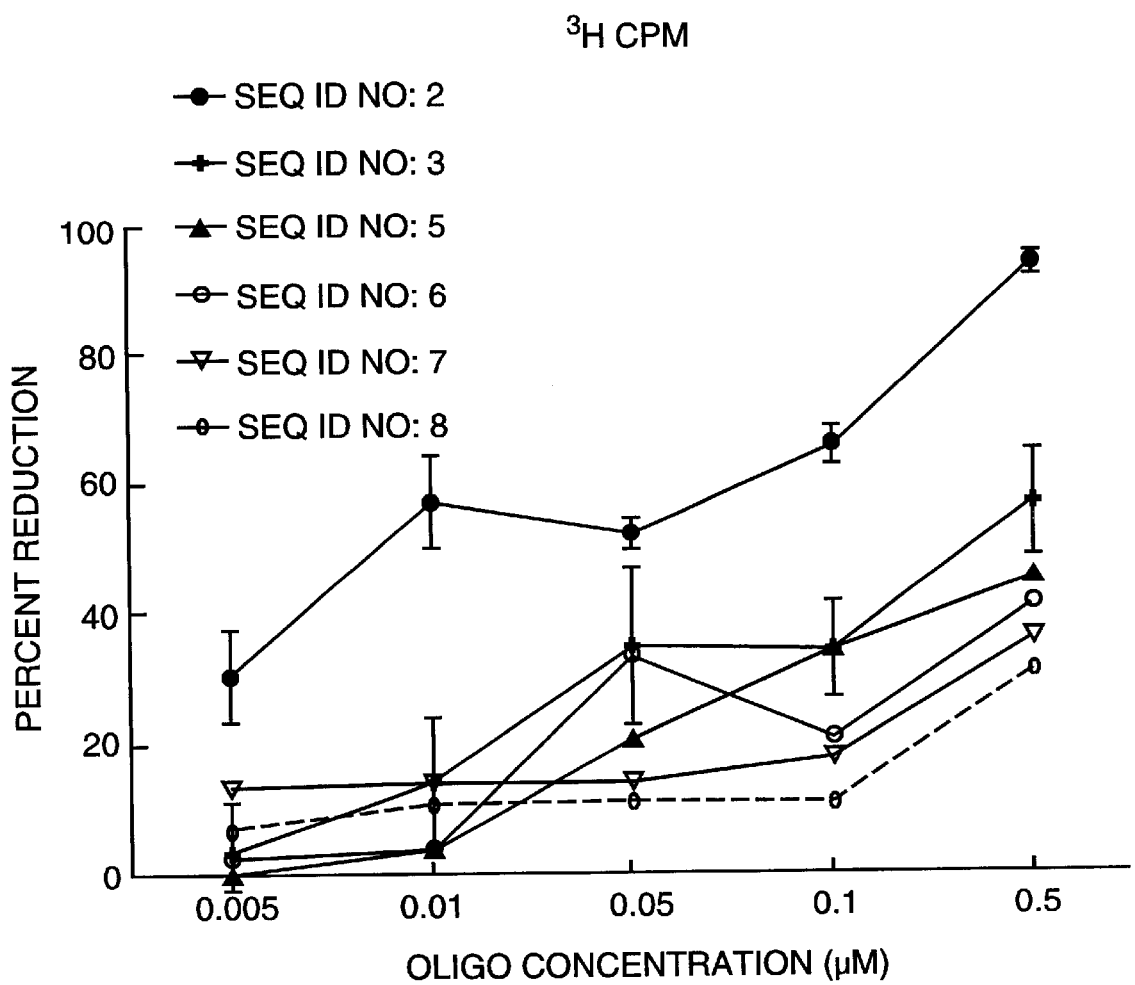
FIG. 1A is a graphic representation showing the inhibition of W2mef parasite growth using an antisense oligonucleotide directed to DHFR ("105", SEQ ID NO:2), and the lack of inhibition of W2mef parasite growth using different concentrations of the following pfmdr1 oligonucleotides: DHFR mismatch control oligonucleotide "RB36" (SEQ ID NO:3); antisense oligonucleotide "RB8" directed to pfmdr1 (SEQ ID NO:5); antisense oligonucleotide "RB9" directed to pfmdr1 (SEQ ID NO:6); antisense oligonucleotide "RB89" targeted to pfmdr1 (SEQ ID NO:7), and antisense oligonucleotide "RB90" directed to pfmdr1 (SEQ ID NO:8).

The patent and scientific literature referred to herein establishes the knowledge that is available to those with skill in the art. The issued U.S. patents, allowed applications, published foreign applications, and references cited herein are hereby incorporated by reference.

Antisense oligonucleotides are used as described herein to reverse the drug resistance phenotype of an infectious organism in cases where acquisition of drug resistance is due to over-expression of either endogenous genes (such as transport genes like mdr), or in cases where the gene conferring resistance has been acquired on a bacterial plasmid (such as beta lactamase). In the case of parasites such as Plasmodium, Leishmania, and Entamoeba, mdr-like genes appear to be involved in drug resistance. It is expected that in all such cases, antisense oligonucleotides specific for mdr nucleic acid would reverse all such resistance. Similarly, oligonucleotides directed to plasmid borne drug resistance genes such as Amp in bacteria would be predicted to reverse resistance to these drugs.

Drug resistance among infectious agents is mediated by at one of least three major mechanisms. The first of these involves mutations in a target gene which alter the ability of a drug to bind to the relevant organism or cell. The second involves mutations in permeases which alter their capacity to import drug into the relevant organism or cell. The third type involves enhanced expression of genes which actively subvert the activity of the relevant drugs, either by facilitating extracellular export or altered internal compartmentalization of the drug (in the case of mdr-like genes), or which actively destroy the drug (in the case of plasmid-borne genes for beta lactamase, as in ampicillin resistance). Mefloquine resistance in malaria may be representative of the third type of mechanism, in that the mdr gene product appears to actively export drug, thereby rendering the parasite resistant.

P. falciparum, one infectious agent which causes malaria in humans, has two homologous mdr genes, designated Plasmodium falciparum multi-drug resistance gene 1 (pfmdr1) and Plasmodium falciparum multi-drug resistance gene 2 (pfmdr2) (Foote et al. (1989) Cell 57:921–930; and Wilson et al. (1989) Science 244:1184–1186). One of these genes, pfmdr1, is believed to encode a P-glycoprotein localized on the digestive vacuole which may mediate efflux of chloroquine from this compartment. The pfmdr1 gene is amplified in some in vitro-derived and clinical isolate chloroquine-resistant and in all mefloquine-resistant strains (Endicott et al. (1989) Ann. Rev. Biochem. 58:137–171); Volkman et al. (1993) Mol. Biochem. Parasitol, 57;203–212). In addition, there is increased expression of pfmdr1-specific mRNA (Volkman et al. (1993) Mol. Biochem. Parasitol. 57:203–212) in both in vitro-derived mefloquine-resistant clones (Oduola et al. (1988) Exp. Parasitol. 67:354–360) and clinical isolates. This information strongly suggests a role for the malarial pfmdr1 gene in resistance to mefloquine, and possibly chloroquine, although other evidence suggest that this is probably not the only mechanism of malarial resistance to chloroquine.

Furthermore, there is considerable clinical evidence for cross resistance to both the structurally related drug quinine and to other structurally unrelated compounds. These observations have been supported by laboratory-based experiments in which W2mef strain parasites placed under high drug pressure also acquire increased resistance to quinine and halofantrine (Peel et al. (1994) Am, J. Trop. Med. Hyg. 51:648–658). These observations all point to a multi-drug resistance-(MDR-) like mechanism (Endicott et al. (1989) Ann. Rev. Biochem. 58:137–71) by which P. falciparum becomes resistant to mefloquine, although until the experiments described herein were performed, definitive proof was lacking. Antisense oligonucleotides used to down-regulate the expression of the pfmdr1 gene have here been shown to reverse the mefloquine-resistant phenotype of parasites, thereby restoring parasite sensitivity to an important antimalarial compound.

Preferably, oligonucleotides used in accordance with the invention have from about 15 to about 50 nucleotides, most preferably from about 17 to about 35 nucleotides, and most preferably, from about 21 to 30 nucleotides. The term "about" as used herein refers to plus or minus one or two nucleotides. Such oligonucleotides are preferably complementary to at least a portion of a targeted genomic region, or gene or an RNA transcript thereof such that the oligonucleotide is capable of hybridizing or otherwise associating with at least a portion of such genomic region, gene, or RNA transcript thereof under physiological conditions. Hybridization is ordinarily the result of base-specific hydrogen bonding between complementary strands of DNA or mRNA transcript preferably to form Watson-Crick or Hoogsteen base pairs, although other modes of hydrogen bonding, as well as base stacking can also lead to hybridization.

Without being limited to any theory or mechanism, it is generally believed that the activity of oligonucleotides used in accordance with this invention depends is on the binding of the oligonucleotide to the target nucleic acid (e.g. to at least a portion of a genomic region, gene or mRNA transcript thereof), thus disrupting the function of the target, either by hybridization arrest or by destruction of target RNA by RNase H (the ability to activate RNase H when hybridized to RNA). Such hybridization under physiological conditions is measured as a practical matter by observing interference with the function of the nucleic acid sequence. Thus, a preferred oligonucleotide used in accordance with the invention is capable of forming a stable duplex (or triplex in the Hoogsteen pairing mechanism) with the target nucleic acid; activate RNase H thereby causing effective destruction of the target RNA molecule, and in addition is capable of resisting nucleolytic degradation (e.g. endonuclease and exonuclease activity) in vivo. A number of the modifications to oligonucleotides described above and others which are known in the art specifically and successfully address each of these preferred characteristics.

The oligonucleotides of the invention which useful in the method and pharmaceutical formulations of the invention are directed to any portion of the pfmdr1 gene that effectively acts as a target for pfmdr1 expression and for reversal of the drug resistant phenotype of Plasmodium parasites. The sequence of the pfmdr1 gene has been reported (Wilson et al. (1989) Science 244:1184–1186; Wilson et al. (1993) Mol. Biochem. Parasitol. 57:151–160; Foote et al. (1989) Cell 57:921–930). Useful target regions (using the nomenclature of Foote et al. (1989) Cell 57:921–930) include conserved regions of the gene (bp 1713 to 2280 and 3977 to 4510), regions adjacent and including the two ATP-binding cassettes (bp 1713 to 1762 and 4468 to 4510), the translational start site (bp 499–502), and species-specific sites (in falciparum, bp 1390 to 1437, 1927 to 2075, 2676 to 2829). A non-limiting list of some useful exemplary pfmdr-specific oligonucleotides are set forth below in Table 1.

TABLE 1

| Oligo (SEQ ID NO:) | Oligo Sequence (5' → 3') | pfmdr Target nucleotides |
|---|---|---|
| 5 | CCATCTTTTTTCTCTTTCTGCTCTTTACC | 3–31 |
| 6 | GGTAATGTTCCTCCTGATAATACAGC | 190–215 |
| 7 | CCTATAGATACTAATGATAATATTATAGG | 277–305 |
| 8 | CGTACCAATTCCTGAACTCACTTGTTC | 478–504 |
| 9 | GGACTATTTATAATAATTCTTGTACC | 1387–4412 |
| 10 | CCCTTCTTTTAGAGTAAAACTTAAATC | 1690–1716 |
| 11 | CCATAATATCTCCTTCGGTTGG | 1792–1813 |
| 12 | CGAAATTAAAGAAAAATTTTTATTTTC | 2120–2146 |
| 13 | CCTGATAATTTGGATGCATTGCTTCC | 2287–2312 |

The oligonucleotides of the invention are composed of ribonucleotides, deoxyribonucleotides, or a combination of both, with the 5' end of one nucleotide and the 3' end of another nucleotide being covalently linked. These oligonucleotides are at least 14 nucleotides in length, but are preferably 19 to 30 nucleotides long, with 20 to 29 mers being the most common.

These oligonucleotides can be prepared by the art recognized methods such as phosphoramidate or H-phosphonate chemistry which can be carried out manually or by an automated synthesizer as described in Uhlmann et al. (*Chem. Rev.* (1990) 90:534–583).

The oligonucleotides of the invention may also be modified in a number of ways without compromising their ability to hybridize to pfrndr mRNA. For example, the oligonucleotides may contain at least one or a combination of other than phosphodiester internucleotide linkages between the 5' end of one nucleotide and the 3' end of another nucleotide in which the 5' nucleotide phosphodiester linkage has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters.

For example, U.S. Pat. No. 5,149,797 describes traditional chimeric oligonucleotides having a phosphorothioate core region interposed between methylphosphonate or phosphoramidate flanking regions. PCT/US96/13371 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various oligonucleotides with modified internucleotide linkages can be prepared according to known methods (see, e.g., Goodchild (1990) *Bioconjugate Chem.* 2:165–187; Agrawal et al., (1988) *Proc. Natl. Acad. Sci.* (USA) 85:7079–7083; Uhlmann et al. (1990) *Chem. Rev.* 90:534–583; and Agrawal et al. (1992) *Trends Biotechnol.* 10:152–158.

The phosphorothioate linkages may be mixed Rp and Sp enantiomers, or they may be stereoregular or substantially stereoregular in either Rp or Sp form (see Iyer et al. (1995) *Tetrahedron Asymmetry* 6:1051–1054). Oligonucleotides with phosphorothioate linkages can be prepared using methods well known in the field such as phosphoramidite (see, e.g., Agrawal et al. (1988) *Proc. Natl. Acad. Sci.* (USA) 85:7079–7083). or by H-phosphonate (see, eg., Froehler (1986) *Tetrahedron Lett.* 27:5575–5578) chemistry. The synthetic methods described in Bergot et al. (*J. Chromatog.* (1992) 559:35–42) can also be used.

Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide.

Other modifications include those which are internal or at the end(s) of the oligonucleotide molecule and include additions to the molecule of the internucleoside phosphate linkages, such as cholesteryl, cholesterol, cholesterol, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3',5'-substituted oligonucleotide having a sugar which, at both its 3' and 5' positions is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O—lower alkyl group containing 1–6 saturated or unsaturated carbon atoms, or with an —O—aryl, or allyl group having 2–6 carbon atoms wherein such —O—alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. None of these substitutions are intended to exclude the native 2'-hydroxyl group in the case of ribose or 2'-H— in the case of deoxyribose. PCT Publication No. WO 94/02498 discloses traditional hybrid oligonucleotides having regions of 2'-O-substituted ribonucleotides flanking a DNA core region. PCT/US96/13371 discloses an "inverted" hybrid oligonucleotide which includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides.

Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides is well known in the art (reviewed in Agrawal et al. (1992) Trends Biotechnol. 10:152–158). For example, nucleotides can be covalently linked using art-recognized techniques such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron Lett.* 28:(31):3539–3542); Caruthers et al. (1987) *Meth. Enzymol.* 154:287–313; U.S. Pat. No. 5,149,798). Oligomeric phosphorothioate analogs can be prepared using methods well known in the field such as methoxyphosphoramidite (see, e.g., Agrawal et al. (1988) *Proc. Natl. Acad. Sci.* (*USA*) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

The synthetic antisense oligonucleotides of the invention are useful in methods for increasing sensitivity of drug-resistant malaria parasites to anti-malarial drugs to which they had otherwise become clinically resistant. These drugs include, but not limited to, mefloquine, quinine, chloroquine, artemesinin, and derivatives thereof. In such methods the parasite is cultured in the presence of a synthetic oligonucleotide complementary to a pfmdr-specific nucleic acid for a time sufficient to enable the oligonucleotide to hybridize to the nucleic acid. Culturing can be done for about 24 to 48 hours, with about 24 hours usually being sufficient. The parasite is then contacted and further cultured with an anti-malarial drug in the presence of the oligonucleotide already added in the first culturing step. The concentration of drug administered will vary depending on the particular drug being administered. For example, for mefloquine and chloroquine, the concentration is in the range of about 1 ng/ml to about 150 ng/ml, and for quinine, the concentration is about 5 ng/ml to 200 ng/ml.

The pfmdr-specific oligonucleotides of the invention are also useful in methods of down-regulating the expression of pfmdr nucleic acid, including the expression of the gene and of the mRNA into protein. In this method, the pfmdr nucleic acid is contacted with a synthetic oligonucleotide, such as one having a nucleotide sequence complementary to a region conserved among malarial parasites, a region surrounding and/or including an ATP binding site, a region including the translational start site, and a region including a sequence specific for a particular species of Plasmodium, such as a *Plasmodium falciparum*-specific region.

There are several methods by which the effects of antisense oligonucleotides on pfmdr expression can be measured. One way is a capture ELISA developed for quantifying pfmdr protein expressed by parasites carrying the gene. At the RNA level, Northern blots (Sambrook et al. (1989) *Molecular Cloning; a Laboratory Manual*, Cold Spring Harbor Laboratory Press, NY, Vol. 1, pp. 7.38; Arcellana-Panlilio et al. (1993) *Meth. Enz.* 225:303–328) can be performed to determine the extent that oligonucleotides of the invention inhibit the expression of pfmdr mRNA.

The synthetic antisense oligonucleotides of the invention may be in the form of a therapeutic composition or formulation useful for treating malaria and for resensitizing drug-resistant parasites to malarial drugs such as, but not limited to, mefloquine and quinine. These oligonucleotides may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of pfmdr expression. For example, combinations of synthetic oligonucleotides, each of which is directed to a different region of the pfmdr nucleic acid, may be used in the pharmaceutical compositions of the invention. The pharmaceutical composition of the invention may further contain other chemotherapeutic drugs for the treatment of malaria, such as quinine, chloroquine, and mefloquine. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-malarial factor and/or agent to minimize side effects of the anti-malarial factor and/or agent.

The pharmaceutical composition of the invention may be in the form of a liposome in which the synthetic oligonucleotides of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323. The pharmaceutical composition of the invention may further include other lipid carriers, such as Lipofectamine, or cyclodextrins and the like which enhance delivery of oligonucleotides into cells, or such as slow release polymers.

As used herein, the term "therapeutically effective amount" means the total amount of each active component of the pharmaceutical composition or method that is sufficient to show a meaningful patient benefit, i.e., a reduction in malarial symptoms. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotides of the invention is administered to a subject afflicted with malaria, or alternatively, as a prophylactic treatment. The synthetic oligonucleotide of the invention may be administered in accordance with the method of the invention either alone or in combination with other known therapies for the malaria. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

It may be desirable at times to use a mixture of different oligonucleotides targeting different conserved sites within the pfmdr1 gene. Such a mixture of oligonucleotides may be in the form of a therapeutic composition comprising at least one, two or more oligonucleotides in a single therapeutic composition (i.e., a composition comprising a physical mixture of at least two oligonudeotides). Alternatively, these oligonucleotides may have two different sequences at times. At least one, preferably two or more oligonucleotides may be administered simultaneously or sequentially as a single treatment episode in the form of separate pharmaceutical compositions.

Administration of the synthetic oligonucleotide of the invention used in the pharmaceutical composition or to practice the method of treating an animal can be carried out in a variety of conventional ways, such as intraocular, oral ingestion, enterally, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, cutaneous or subcutaneous injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 1.0 ng to about 2.5 mg of synthetic oligonucleotide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the synthetic oligonucleotide will be in the range of 12 to 24 hours of continuous intravenous administration. Ultimately the attending physician will decide on the appropriate duration of intravenous therapy using the pharmaceutical composition of the present invention.

The oligonucleotides of the invention may also be a part of kits for resensitizing an anti-malarial drug-resistant Plasmodium parasite to an anti-malarial drug or for downregulating the expression of pfmdr nucleic acid in a cell. Such a kit includes a synthetic oligonucleotide specific for pfmdr nucleic acid, such as those described herein. For example, the kit may include at least one of the synthetic contiguous oligonucleotides of the invention, such as, but not limited to, those having SEQ ID NO: 5–13. These oligonucleotides may have modified backbones, such as those described above, and may be RNA/DNA hybrids containing, for example, at least one 2'-O-methyl. The kit of the invention may optionally include buffers, cell or tissue preparation reagents, cell or tissue preparation tools, vials, and the like.

Laboratory techniques for in vitro screening of antimalarial drugs are well known in the art. Such techniques utilize the asexual erythrocytic cycle of *P. falciparum* in cultured human red blood cells. Trager (*Science* (1976) 193:673–675) discloses continuous maintenance of human malarial parasites in vitro. Desjardins et al. (*Antimicrobial Agents Chemother.* (1979) 16:710–718) discloses a method a quantitative assessment of the in vitro antimalarial activity of drugs, using a semiautomated microdilution technique. Chulay et al. (*Expt. Parasitol.* (1983) 55:138–146) discloses a method of assessing in vitro growth of *P. falciparum* by measuring incorporation of [$^3$H]-hypoxanthine. Lambros et al. (*J. Parasitol.* (1979) 65:418–420) discloses procedures for the synchronization of the erythrocytic stages of *P. falciparum* in culture, which allows mechanistic interpretation of the activities of antimalarial drugs.

These in vitro systems have been shown to be predictive of the clinical outcome for a variety of agents in the treatment of human malaria. Bitonti et al. (*Science* (1988) 242:1301–1303) discloses correct in vitro prediction of reversal of chloroquine resistance in *P. falciparum* by desipramine. Martin et al. (*Science* (1987) 235:899–901) discloses correct in vitro prediction of the reversal of chloroquine resistance in *P. falciparum* by verapamil.

With the use of such screening techniques, the effect of antisense oligonucleotides directed to pfmdr1 was examined in the absence of mefloquine. Mefloquine-resistant parasites (W2mef) were cultured in the presence of anti-pfmdr1 oligonucleotides which included a positive control (oligonucleotide 2 having SEQ ID NO:2) directed against the parasite dihydrofolate reductase-thymidylate synthase (DHFR), previously had been shown to be highly inhibitory of parasite growth (Barker et al. (1996) *Proc. Natl. Acad. Sci. USA*) 93:524–528)), negative controls consisting of an oligonucleotide targeted to HIV (SEQ ID NO:1) which shares no known homology with *P. falciparum*, and DHFR mismatch controls (SEQ ID NOS:3 and 4). Cells were then cultured in the presence of $^3$H-hypoxanthine before harvesting. The results in FIG. 1A showed that antisense oligonucleotides directed to complementary to DHFR were not inhibitory to parasite growth in the absence of mefloquine.

Figure 1B:
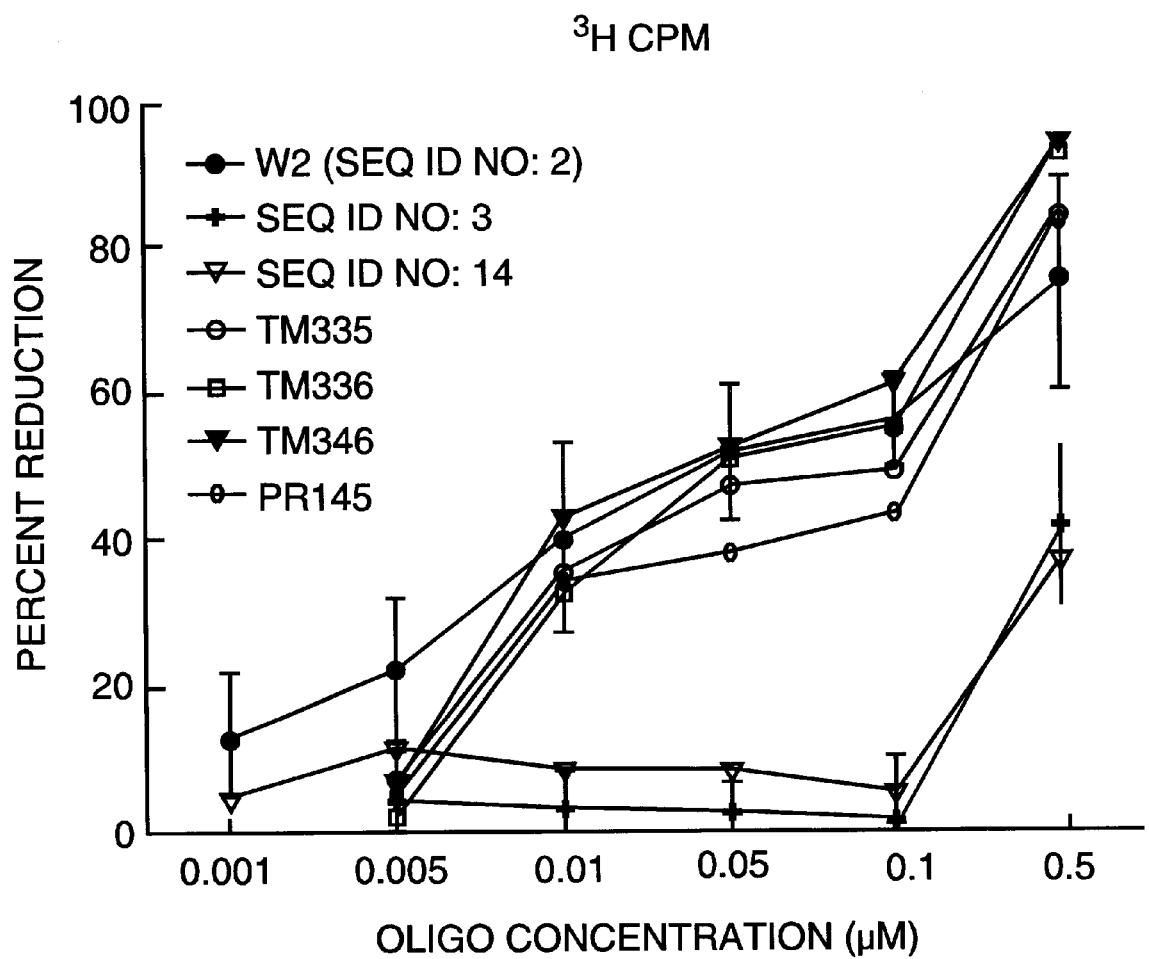
FIG. 1B is a graphic representation showing anti-malarial specificity of a pfmdr1-specific oligonucleotide of the invention in W2 parasites and in various field isolate strains, wherein "W2" refers to W2 strain parasites treated with an anti-DHFR oligonucleotide 105 (SEQ ID NO:2); "RB36" refers to W2 parasites (sensitive to mefloquine) treated with an anti-DHFR mismatch control oligonucleotide (SEQ ID NO:3); "RB58" refers to W2 parasites treated with a DHFR sense strand oligonucleotide (SEQ ID NO:14); and TM335, TM336, TM346, and PR145 are field isolate strains treated with the DHFR-specific antisense oligonucleotide 105 (SEQ ID NO:2).

Equivalent experiments were performed using mefloquine-resistant, naturally occurring field isolate parasites (PR145, TM336, TM346, and TM352) and mefloquine-sensitive strain TM335. FIG. 1B shows that antisense oligonucleotides specifically targeted to malarial genes do get into parasites, and do specifically inhibit growth. Thus, failure by anti-pfmdr1 antisense oligonucleotides to inhibit is not due to a failure in uptake. The results shown in FIG. 1B also demonstrate that both drug-sensitive and multi-drug resistant field isolates were equally sensitive to the inhibitory effects of anti-sense oligonucleotides directed to pfmdr1, suggesting that uptake of oligonucleotides in these strains is similar to that seen in the laboratory strains.

Experiments were then done to examine whether the mefloquine resistant phenotype could be altered by exposure of parasites to different amounts of oligonucleotides targeted to pfmdr1. W2mef strain *P. falciparum* parasites were exposed to varying concentrations of mefloquine either in the presence or absence of oligonucleotides directed to pfmdr1.

Figure 2:
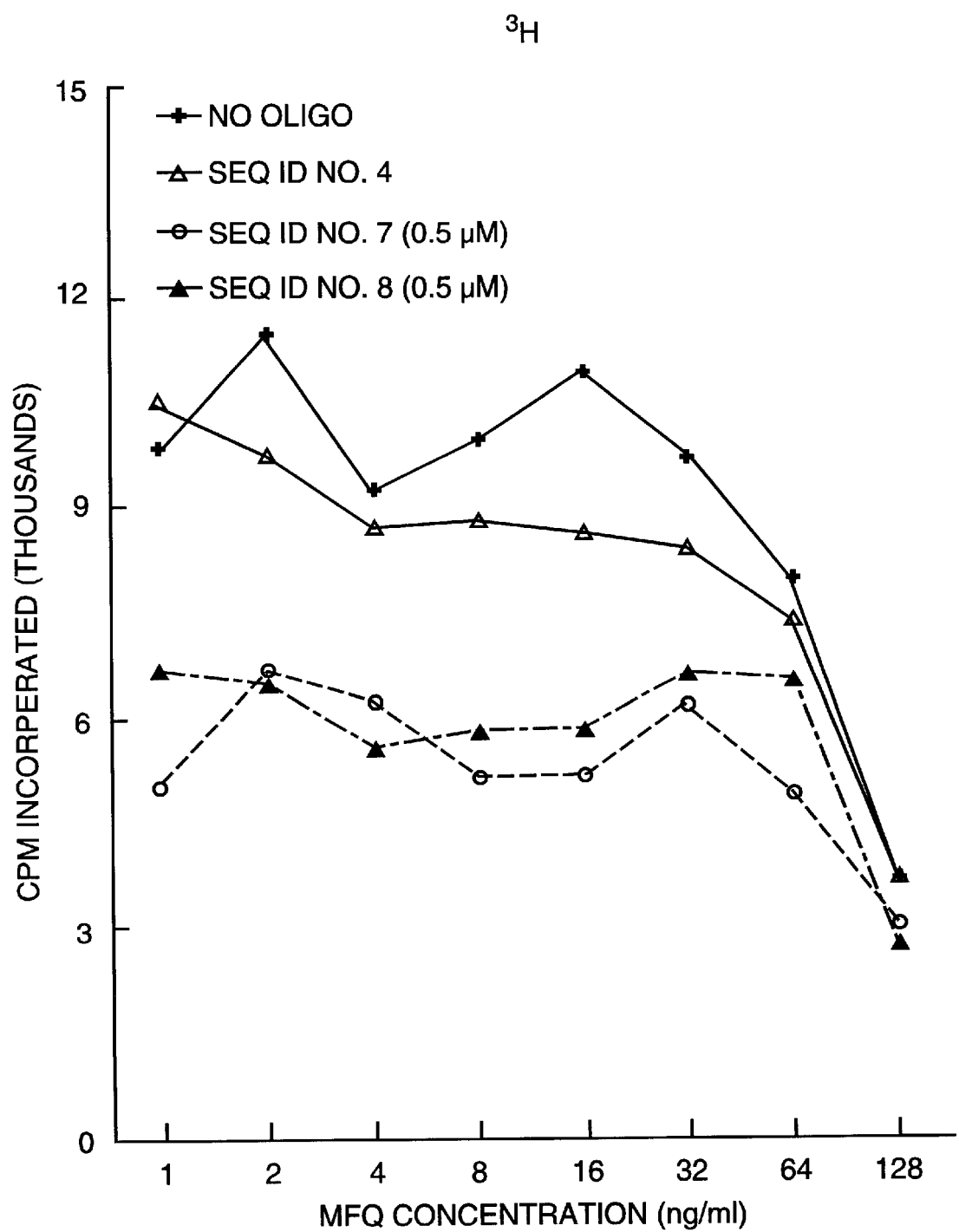
FIG. 2 is a graphic representation showing reversal of mefloquine (MFQ) resistance in W2mef parasites (resistant to mefloquine) after treatment in the presence or absence of 0.5 $\mu$M oligonucleotides ("RB37" a mismatch control oligonucleotide directed to DHFR (SEQ ID NO:4); "RB89", an antisense oligonucleotide directed to pfmdr1 (SEQ ID NO:7); and "RB90," an antisense oligonucleotide directed to pfmdr1 (SEQ ID NO:8), followed by mefloquine at the concentrations indicated, where resistance is measured by the incorporation of $^3$H-hypoxanthine into the cells.
Figure 3:
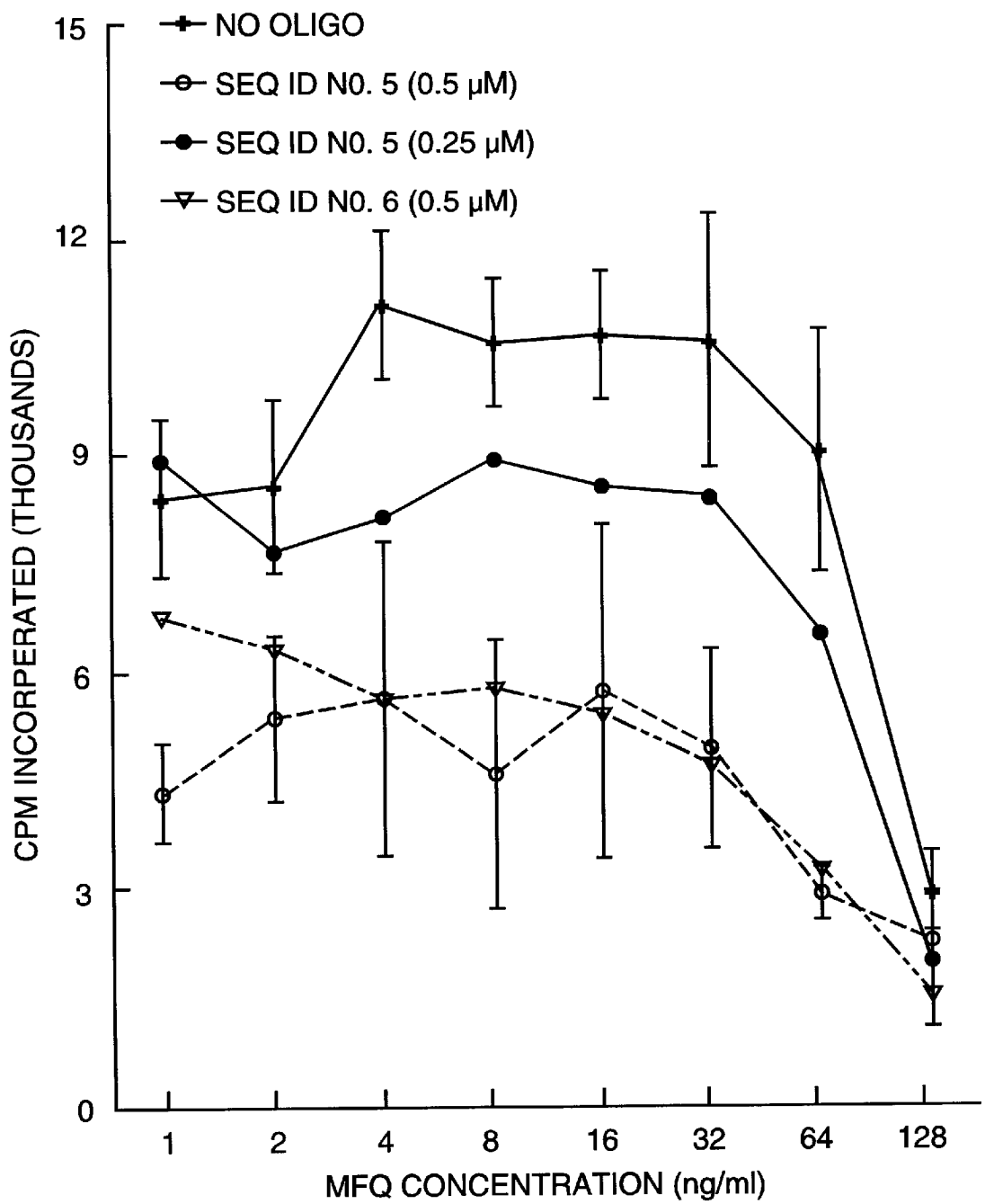
FIG. 3 is a graphic representation of the reversal of mefloquine resistance in W2mef parasites after treatment with 0.25 $\mu$M or 0.5 $\mu$M anti-pfmdr1 oligonucleotide having SEQ ID NO:5 or 6, followed by different concentrations of mefloquine as described in FIG. 2 above.
Figure 4:
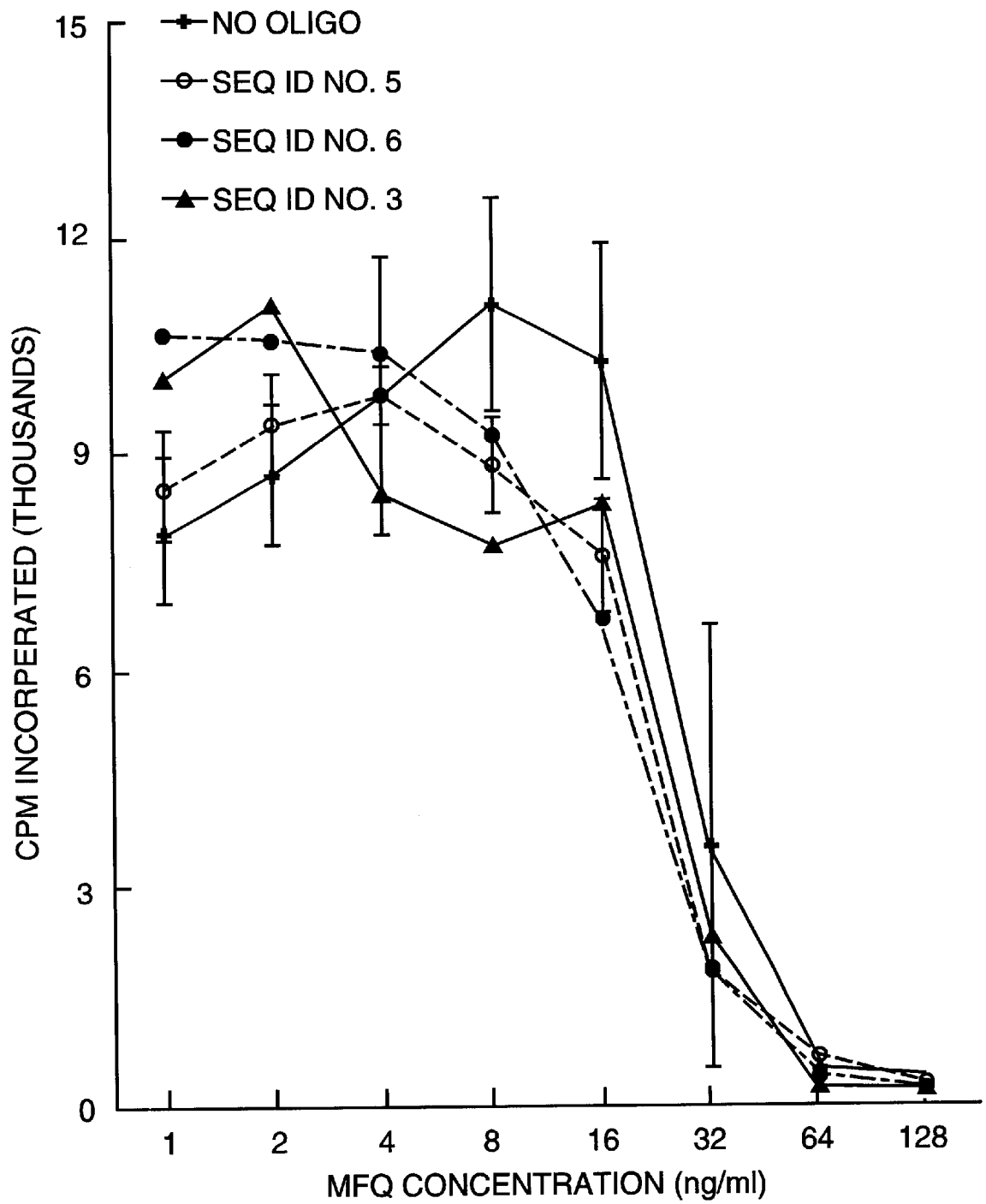
FIG. 4 is a graphic representation of the unaltered sensitivity of W2 parasites in the presence or absence of 0.5 $\mu$M anti-pfmdr1 oligonucleotide RB8 (SEQ ID NO:5), anti-pfmdr1 oligonucleotide RB9 (SEQ ID NO:6), or anti-DHFR mismatch control oligonucleotide RB36 (SEQ ID NO:3) to different concentrations of mefloquine, as described in FIG. 2.

The results in FIGS. 2–4 show that W2mef strain parasites exposed to mefloquine alone without oligonucleotides specific for pfmdr1 incorporated on average 11,000 cpm $^3$H-hypoxanthine until the mefloquine concentration exceeded 32 ng/ml. As the mefloquine concentration increased, $^3$H incorporation rapidly fell (FIG. 2). W2mef parasites exposed to mefloquine in the presence of 0.5 μM oligonucleotide 3 (SEQ ID NO:3), a DHFR-specific mismatch control oligonucleotide, incorporated on average 9,000 cpm $^3$H-hypoxanthine until mefloquine concentrations exceeded 64 ng/ml, a level of incorporation which did not differ significantly from that of parasites exposed to mefloquine alone (FIG. 2).

However, W2mef strain parasites treated with 0.5 μM oligonucleotide having SEQ ID NOS:5–7 all showed approximately 50% inhibition of growth in the presence of mefloquine (FIGS. 2 and 3), in contrast to parasites treated with a control oligonucleotide having SEQ ID NO:4, indicating the sequence-specific effect of the antisense oligonucleotides specific for pfmdr1, resulting in increased sensitivity to drug. This effect was also proportional to oligonucleotide concentration (FIG. 3), and was more pronounced at higher oligonucleotide concentrations. Similar results were obtained with oligonucleotides with SEQ ID NOS:6, 7, and 8 targeted to pfmdr1.

When similar experiments were done with W2, a mefloquine-sensitive sister clone of W2mef, the results were quite different. Neither oligonucleotide targeted to pfmdr1 (oligonucleotide 5 or 6) or mismatch control oligonucleotide (SEQ ID NO:3) induced statistically significant increases in sensitivity to mefloquine (FIG. 4).

Figure 5:
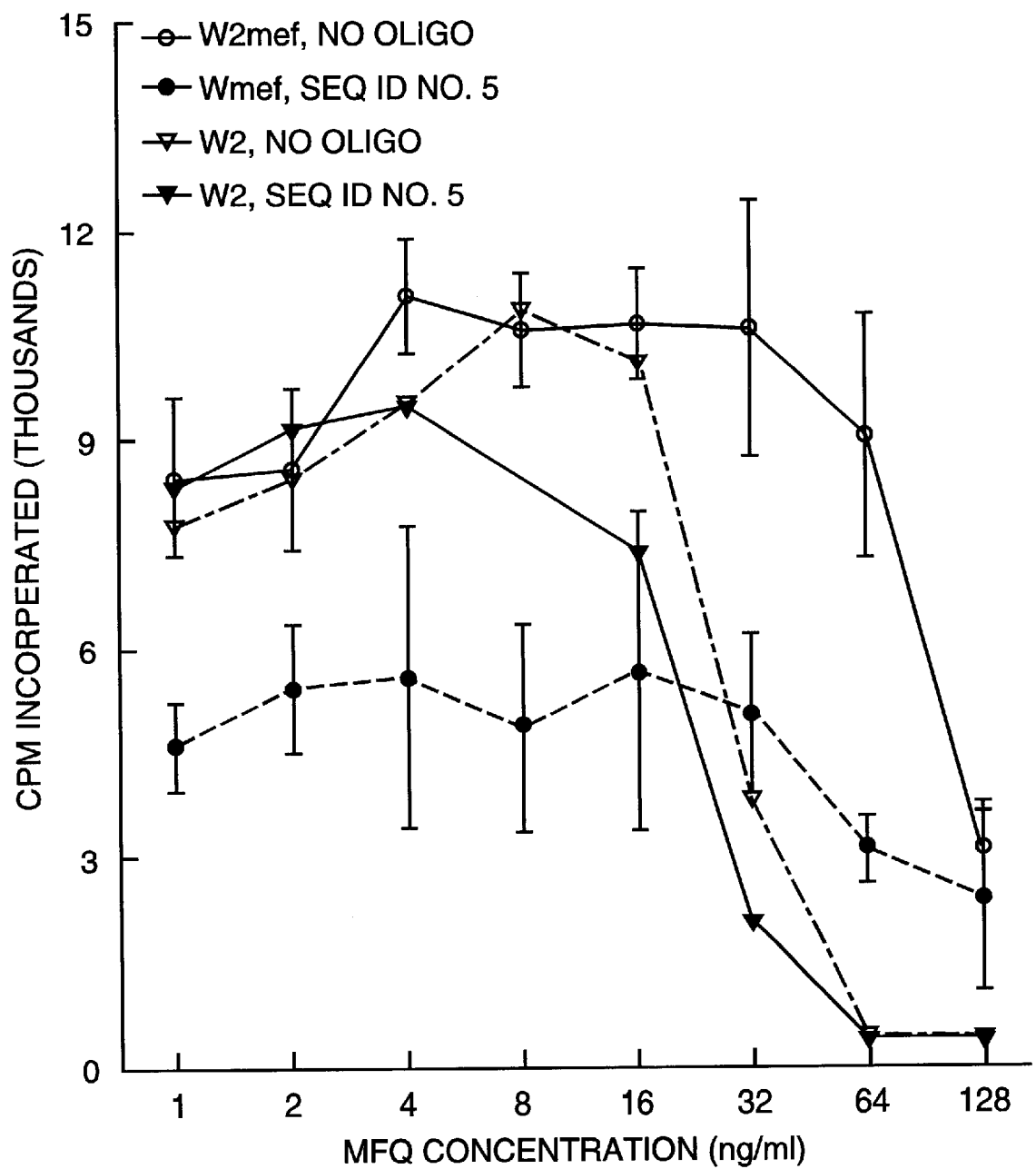
FIG. 5 is a graphic representation summarizing data showing the reversal of mefloquine resistance in W2mef (resistant to mefloquine), but not W2 parasites (sensitive to mefloquine) in the absence or presence of the RB8 anti-pfmdr1 oligonucleotide (SEQ. ID NO:5) and different concentrations of mefloquine.

Results from these experiments are summarized in FIG. 5, which shows both W2 or W2mef exposed to mefloquine in the absence of oligonucleotide directed to pfmdr1, or after incubation with 0.5 μM oligonucleotide. The effect of altered sensitivity to mefloquine can be seen in two ways. There is a 50% reduction in overall hypoxanthine incorporation by W2mef in the presence of mefloquine when antisense oligonucleotides specific for pfmdr1 are present, and the threshold sensitivity is shifted downwards from approximately 32 ng/ml to 16 ng/ml. In contrast, the sensitivity of the W2 strain to mefloquine does not change significantly in the presence of oligonucleotide specific for pfmdr1.

Figure 6:
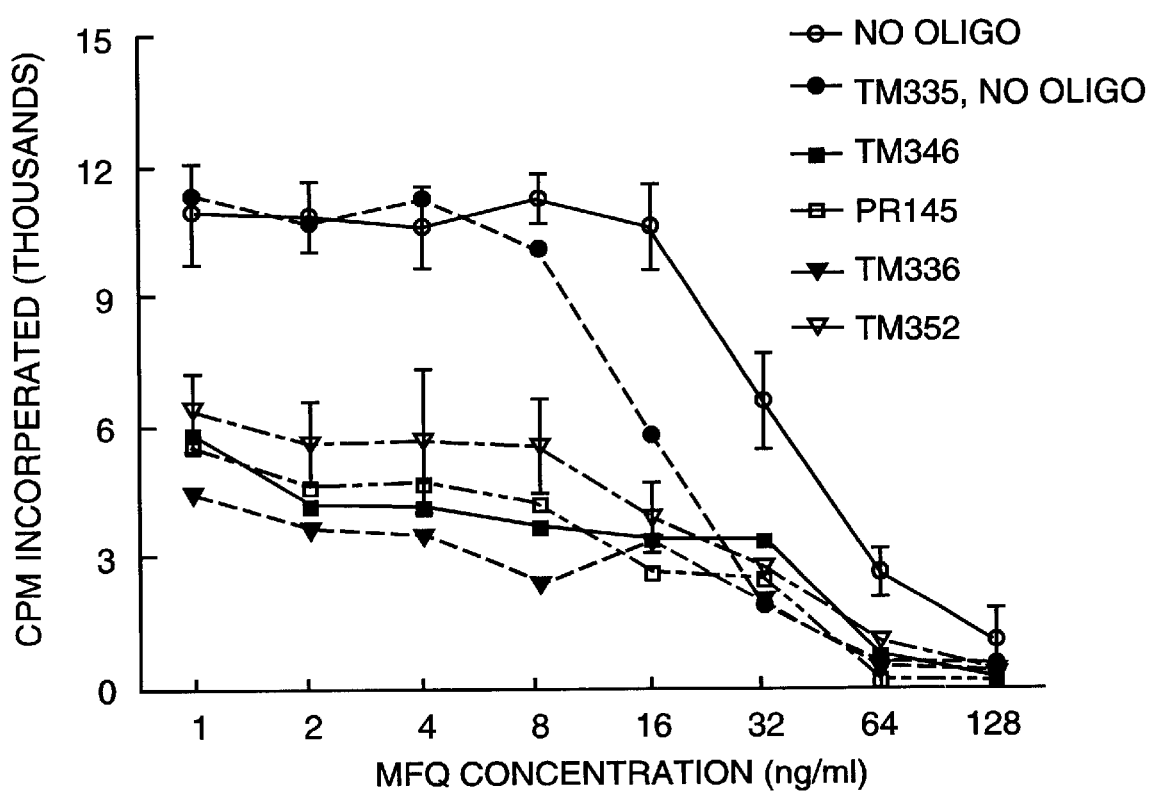
FIG. 6 is a graphic representation of the reversal of mefloquine resistance in field isolates TM335, TM346, PR145, TM336, and TM352 treated with and without 0.5 $\mu$M RB90 anti-pfmdr1 oligonucleotide (SEQ ID NO:8) in the presence of varying concentrations of mefloquine, wherein values for all untreated mefloquine-resistant field isolates were averaged.

Similar experiments were done using field isolates TM336, TM346, TM352 and PR 145 to determine if oligonucleotides directed to pfmdr1 could reverse resistance to mefloquine. The results shown in FIG. 6 show that for each mefloquine-resistant strain, both total incorporated CPM and $IC_{50}$ were reduced in the presence of anti-pfmdr1 oligonucleotides of the invention plus mefloquine.

These experiments demonstrate that in the presence of oligonucleotides specific for pfmdr1, W2mef, a mefloquine-resistant strain of P. falciparum, becomes significantly (P<0.05) more sensitive to mefloquine. This can be seen both by reduced total incorporation of $^3$H-hypoxanthine, and in the downward shift in the threshold dose at which the parasite loses tolerance to mefloquine. These effects are specific, since mismatch control oligonucleotides do not significantly alter mefloquine sensitivity FIGS. 2 and 4). Thus, these studies also show that reduced $^3$H-hypoxanthine incorporation is due to the effect of specific oligonucleotides in the presence of mefloquine, since neither mismatch control oligonucleotides nor oligonucleotides specific for pfmdr1 significantly inhibit parasite growth (FIG. 1). These studies further demonstrate that mefloquine resistance in field isolates can be reversed in the presence of antisense oligonucleotides specific for pfmdr1.

Increased resistance to mefloquine in both laboratory isolates (Wilson et al. (1993) Mol. Biochem. Parasitol. 57:151–160; and Peel et al. (1994) Am. J. Trop. Med. Hyg. 51:648–658) and in clinical studies (Brasseur et al. (1992) Am. J. Trop. Med. Hyg. 46:1–7; Brasseur et al. (1992) Am. J. Trop. Med. Hyg. 46:8–14; Suebsaeng et al. (1986) Bull. WHO 64:759–765; Cowman et al. (1994) Proc. Natl. Acad. Sci. (USA) 91:1143–1147), has also been accompanied by increased resistance to halofantrine and quinine. If cross resistance is mediated by an mdr-like mechanism, inhibition of pfmdr1 by antisense oligonucleotides would also reduce levels of resistance to halofantrine and quinine.

Figure 7:
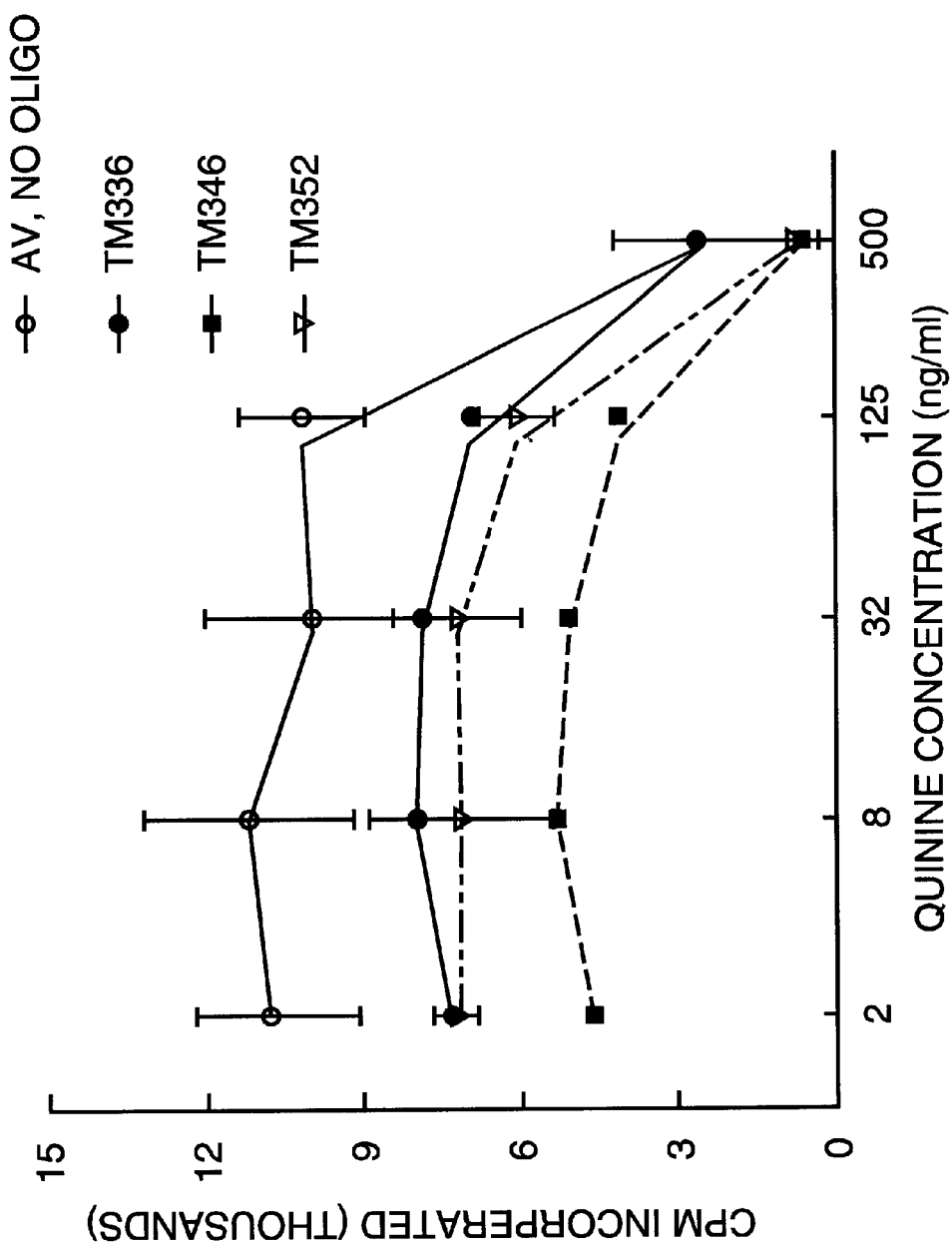
FIG. 7 is a graphic representation of the reversal of quinine resistance in field isolates TM336, TM346, and TM352 treated with or without 0.5 $\mu$M anti-pfmdr1 oligonucleotide RB90 (SEQ ID NO:8) in the presence of varying concentrations of quinine, wherein values for all untreated quinine-resistant field isolated were averaged.
Figure 8:
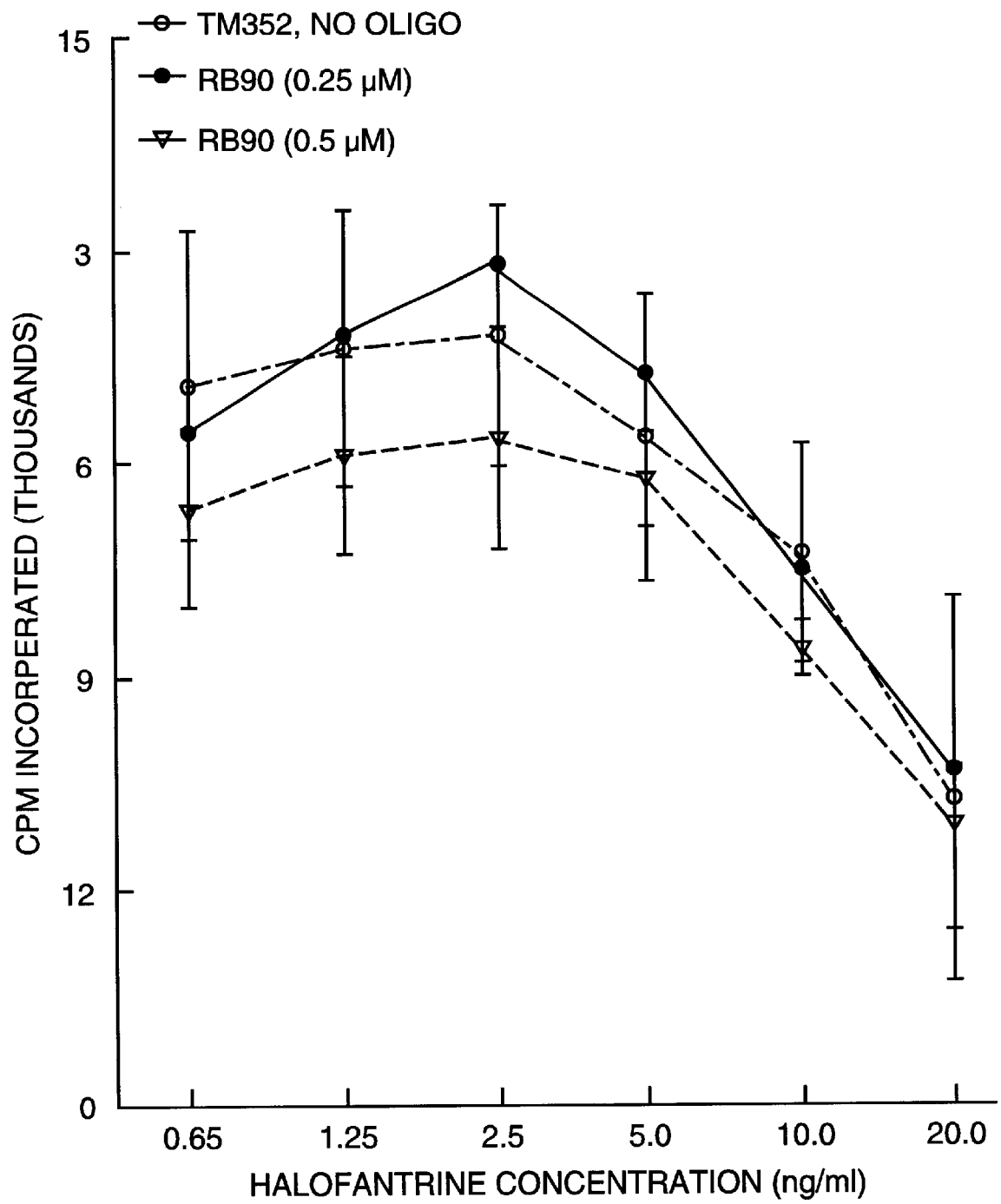
FIG. 8 is a graphic representation of the lack of reversal of halofantrine resistance in a field isolate TM352 treated with 0.25 $\mu$M or 0.05 $\mu$M RB90 anti-pfmdr1 oligonucleotide (SEQ ID NO:8) or without oligonucleotide.

As shown in FIG. 7, all four field isolates tested showed altered responses to quinine when exposed to drug in the presence of an oligonucleotide of the invention directed to pfmdr1. In all cases there was a reduction in total cpm incorporated and in the $IC_{50}$ in the presence of antisense oligonucleotides of the invention. One isolate (TM336) showed a concentration-dependent response, with greater sensitivity to quinine in the presence of 0.5 μM of drug. Antisense oligonucleotides directed to pfmdr1 appear not to affect halofantrine resistance under these conditions.

The present studies demonstrate that resistance to quinine can be reduced in the presence of oligonucleotides targeted specifically against pfmdr1. These results therefore indicate that the malarial mechanism of resistance to quinine is similar to that for mefloquine, since the same (or very similar) gene product(s) appear to be required for both. In conclusion, antisense oligonucleotides of the invention directed against pfmdr1 can be used to modulate resistance to both mefloquine and quinine, and can be the basis for a clinical method for restoring sensitivity to these drugs.

Techniques for in vivo screening of anti-malarial drugs are also known in the art. For example, splenectomized monkeys (Peters, Chemotherapy and Drug Resistance in Malaria. (1987) London: Academic Press, pp. 217–239) and unsplenectomized rodents such as mice have been developed to study malaria (Peters (1965) Exp. Parasitol. 17:89–90; Peters et al. (1977) Ann. Trop. Med. Parasitol. 71:419–427). These rodents are susceptible to a similar species of parasite, P. berghei. Like P. falciparum in humans, resistance in rodents may be modulated at least in part by an mdr-like mechanism. Using such a model, it has been shown that there is decreased chloroquine accumulation in chloroquine-resistant P. berghei parasites (Macomber et al. (1966) Science 235:1365–1372), and that resistance can be reversed using verapamil (Valecha et al. (1992) Ind. J. Malariol. 29:47–53). Similar results were obtained in P. chabaudi in the case of chloroquine resistance (Miki et al. (1992) Exp. Parasitol. 72:134–142). It has also been shown for P. berghei that mefloquine resistance can be reversed using penfluoridal, thereby confirming results obtained using P. falciparum in vitro. At the molecular level, the mdr gene homologs in P. berghei and P. yoelli have been cloned and sequenced.

To determine whether antisense oligonucleotides can be used in vivo to inhibit malarial growth, a chicken (P. gallinaceum) malarial model was used. This model was chosen because the pathology of the host associated with infection by P. gallinaceum is very similar to that found in human malarias, indicating that it is a particularly useful model for P. falciparum infection. At a molecular level, genetic analysis has shown that this species is much more closely related to the human parasite P. falciparum than are other non-human infecting species such as the rodent malarias (Walliker et al. (1987) Science 236:1661–1666). Also, very high parasitemias are obtained using the P. gallinaceum model. The proportion of infected erythrocytes typically reaches 60–80% before becoming lethal to the host, enabling a broad range over which measurements of the effects of drug treatment can be taken. Experiments were designed using DHFR-specific antisense oligonucleotides known to inhibit the growth of parasites in vitro. Results obtained using this in vivo model indicate that antisense oligonucleotides directed to DHFR increase the survival rate and decrease parasitemia. These results are the first obtained showing the efficacy of antisense oligonucleotides against malaria in vivo. They indicate that for inhibition of parasite growth, the earlier in vitro experiments using antisense oligonucleotides were good predictors of results from subsequent work performed in vivo. It now seems probable that the in vitro results for drug resistance reversal described herein will also be predictive of results to be obtained using an in vivo model.

The following examples illustrate the preferred modes of making and practicing the present invention, but are not meant to limit the scope of the invention since alternative methods may be utilized to obtain similar results.

EXAMPLES

1. Preparation of Parasite Strains

*P. falciparum* strains W2 and W2mef were originally developed by Oduola and coworkers (Oduola et al. (1988) *Exp. Parasitol.* 67:354–360). W2 was cloned from a chloroquine-resistant Indochina isolate by sequential passages at limiting dilution, then was placed under step-wise mefloquine pressure. The resulting mefloquine-resistant daughter clone W2mef was then recloned, resulting in a matched pair of strains (W2 and W2mef) isogenic in all respects except mefloquine resistance.

*P. falciparum* strains were maintained by a modification of the method of Trager et al. (*Science* (1976) 193:673–675), using supplemented RPMI (GIBC0 Laboratories, Grand Island, N.Y.) medium. For conventional culture this contained (in 500 ml RPMI): 1 g sodium bicarbonate (Sigma Chemicals, St. Louis, Mo.), 1.5 g TES (N-tris[hydroxymethyl]-methyl-2-aminoethane-sulfonic acid) sodium salt (Sigma), 1 g glucose (Sigma), 5 ml 3% glutamine (Sigma), 5 ml 1.1% pyruvate (Sigma), and 5 ml 0.05% hypoxanthine (Sigma), 50 ml human type A+ plasma (American Red Cross Blood Services, Dedham, Mass.), 0.25 ml gentamicin (Sigma) and 5% (v/v) human type A+ red blood cells (Red Cross) at 37° C. in 2% $O_2$, 8% $CO_2$. RPMI was routinely prepared containing bicarbonate, TES, and glucose, then filtered through 0.22 micron filter. Pyruvate, hypoxanthine, and glutamine were prepared as stock solutions (concentrations given above), were aliquotted 6 ml/tube, and were stored frozen at −20° C. Human type A+ plasma was pooled from at least 8 donors, aliquotted 51 ml/tube, and stored at −20° C. Type A+ red blood cells were obtained and used fresh (within one month of collection. Before use, they were washed 2× by centrifugation in RPMI. The final pellet was resuspended in an equal volume of supplemented RPMI. W2mef strain parasites were routinely cultured in the presence of 10 ng/ml mefloquine to maintain mefloquine pressure.

Clinical isolates for these experiments were obtained from Dr. Dyann Wirth, Harvard School of Public Health. These strains were originally isolated By Dr. Sodsri Thaithong (Wilson et al. (1993) *Mol. Biochem. Parasitol.* 57:151–160) from patients presenting at the Tropical Medicine Hospital or the Malaria clinic at Pong Nam Ron in Chataburi province, Thailand. Isolates were stabilized in RPMI medium, then transported back to the laboratory at the WHO Collaborating Center, Chulalongkorn University, in Bangkok, where they were maintained in in vitro culture as described above. Original drug susceptibility testing was done both in the lab at Chulalongkorn, and in parallel at the Walter Reed Army Institute of Research in Washington, D.C. Results from these susceptibility tests are shown below in Table 2 (Wilson et al. (1993) (*Mol. Biochem. Parasitol.* 57:151–160).

TABLE 2

| Strain | $IC_{50}$ (ng/ml) | | |
|---|---|---|---|
| | MFQ | Quin | HAL |
| W2mef | 16 | N.D. | N.D. |
| W2 | 2 | 74 | 0.3 |
| TM335 | 6 | 65 | 0.61 |
| PR145 | 10 | 90 | 2.0 |
| TM336 | 15 | 87 | 2.8 |
| TM346 | 20 | 114 | 3.7 |
| TM352 | 22 | 1.2 | 3.0 |
| sensitive: | <8 | <25 | N.D. |

MFQ: mefloquine
QUI: quinine
HAL: halofantrine

These results indicate a range of sensitivity to both mefloquine and quinine: strain TM335 is approximately the same sensitivity as W2, whereas strains PR145, TM336, TM346, and TM 352 are mefloquine-resistant. TM336, TM346 and TM352 field isolates were routinely cultured in the presence of 10 ng/ml mefloquine to maintain mefloquine pressure.

2. Oligonucleotide Preparation

Antisense oligonucleotides were synthesized on a Biosearch model 8700 synthesizer (Milligen, Bedford, Mass.). Assembly of oligonucleotides was performed using standard phosphoramidite chemistry. Phosphorothioate bonds were introduced by oxidation with the Beaucage thiolating reagent (Iyer et al. (1990) *J. Am. Chem. Soc.* 112:1253–1254) as previously described (Padmapriya et al. (1994) *Antisense Res. Dev.* 4:185–199). Full length oligonucleotides were purified by HPLC and final purity was assayed by HPLC using a WAX column (Metelev et al. (1992) *Anal. Biochem.* 200:342–346). Oligonucleotides were lyophilized and then resuspended in glass distilled water to 0.5 mM. Before use in vitro, 10 μM oligonucleotide working solutions were prepared by dilution in unsupplemented RPMI lacking human plasma, and were filter sterilized through a 0.45 μm filter. Additional working solutions (1 μM and 0.1 μM were then prepared by serial 10-fold dilution in plasma-free RPMI. for charging microtiter plates.

The sequences of the oligonucleotides used is shown in Table 3.

TABLE 3

| Oligo (SEQ ID NO:) | Sequence (5' ← 3') | Target |
|---|---|---|
| 1 | TCTTCCTCTCTCTACCCACGCTCTC | HIV gag |
| 2 | TCTTAAAAATAATTTCTTCGTAGTTAA | DHFR |
| 3 | TCATATAATTATTTACTACGTTGTAAA | DHFR |
| 4 | TGTTATATAAAAATTGTTCCTACTTTT | DHFR |
| 5 | CCATCTTTTTCTCTTTCTGCTCTTTACC | pfmdr1 |
| 6 | GGTAATGTTCCTCCTGATAATACAGC | pfmdr1 |
| 7 | CCTATAGATACTAATGATAATATTATAGG | pfmdr1 |
| 8 | CGTACCAATTCCTGAACTCACTTGTTC | pfmdr1 |
| 14 | TTACTACGAAGAAATTATTTAAGA | DHPR* |

"_ denotes mismatched bases
*sense strand complimentary to SEQ ID NO:2.

Oligonucleotide 1 (having SEQ ID NO:1) is directed to the gag gene of HIV1 (Lisziewicz et al. (1994) *Proc. Natl. Acad. Sci. USA,* 1994 91:7942–7946, and is used as a (negative) sequence control. The RB105 oligonucleotide (having SEQ ID NO:2) is directed to a conserved sequence in the thymidylate synthase portion of the DHFR gene from bp 1153–1179 (Bzik et al. (1987) *Proc. Acad. Sci. USA*

84:8360–8364), and was used as a positive control for inhibition of parasites. The RB36 oligonucleotide (having SEQ ID NO:3) was derived from the oligonucleotide 1 sequence, but contains eight mismatches, and is used as a negative control. Use of these sequences to specifically inhibit *P. falciparum* strains has been previously described (Barker et al. (1996) *Proc. Natl. Acad. Sci. USA*, 93:514–518). The RB58 oligonucleotide (having SEQ ID NO:14) is directed to the sense strand of the DHFR gene. Oligonucleotides 5–8 (RB8, RB9, RB89, and RB90, respectively) having SEQ ID NOS:5–8, respectively) are directed to pfmdr1 as described in Wilson et al. (1989) *Science* 244:1184–1186 (GenBank Accession No. M24850). Oligonucleotide 5 targets the 5' region at bp 3–32; oligonucleotide 6 targets a sequence at bp 190–215; oligonucleotide 7 targets a sequence at bp 277–305, and oligonucleotide 8 targets bp 478–504.

3. Parasite Inhibition Assays

Effects of oligonucleotides on parasite growth was measured either by microscopic examination of thin smears or by $^3$H-hypoxanthine incorporation after drug treatment. For microscopy, 48-well microtiter plates were charged with oligonucleotides at different dilutions. Unsynchronized parasites were added to a total of 1 ml (0.4% parasitemia, 5% red blood cells) and were cultured 24 hr at 37° C. in supplemented RPMI medium as described above. Slides were prepared and were stained using the Diff-Quick™ staining procedure (Baxter Healthcare Corp., McGraw Park, Ill.) according to the manufacturer's instructions. To determine the proportion of infected cells, at least 500 red blood cells were counted. Results were expressed as percent reduction compared with controls receiving medium alone without oligonucleotides.

Hypoxanthine incorporation assays measuring parasite inhibition were based on those described by Desjardins and coworkers (Desjardins et al. (1979) *Antimicrob. Agents Chemother.* 16:710–718). Initial experiments examined the effects of antisense oligonucleotides alone, in the absence of mefloquine. For these experiments, 96 well microtiter plates were charged with either 10 µl or 20 µl of each working solution of oligonucleotides, to yield final concentrations of 0.5 µM, 0.1 µM, 0.05 µM, 0.01 µM, and 0.005 µM oligonucleotide. Four wells were used for each dilution. Control wells received 10 µl or 20 µl of plasma-free RPMI without oligonucleotides. Two hundred µl of unsynchronized parasites were then added (0.4% parasitemia, 5% red blood cells), and cultures were incubated at 37° C. After 20–24 hr, 0.5 µCi [$^3$H(G)]-hypoxanthine (10–30 Ci/mmol, New England Nuclear, Boston, Mass.) was added to each well, cultures were incubated overnight, and cells were harvested for scintillation counting using a PHD cell harvester (Cambridge Technology, Inc, Watertown, Mass.). Harvesting consisted of lysing cells and washed 3 times (200 µl/well each wash) with distilled water, and filtering onto glass fiber filters (Cambridge Technology). Filters were air-dried overnight, resuspended in 5 ml Ecolume™ scintillation cocktail (ICN Biomedicals, Costa Mesa, Calif.), and the cpm measured. After counting, values were averaged for the four samples at each dilution, the average was multiplied by the proportion of parasites present at that dilution of oligonucleotides relative to control (determined by microscopy), and then was expressed as percent reduction compared with control samples receiving no oligonucleotides. Representative results are shown in FIG. 1A (clinical isolates) and FIG. 1B (field isolates).

4. Mefloquine Resistance Reversal Studies

For mefloquine resistance reversal experiments, 5 µl or 10 µl of the 10 µM working solution of oligonucleotide was aliquotted into wells 96-well of microtiter plates to yield final oligonucleotide concentrations of 0.25 µM or 0.5 µM after addition of parasites. Control wells received 5 µl or 10 µl RPMI alone, without oligonucleotides. Two hundred µl of unsynchronized parasites deleted in modified RPMI (0.4% infected erythrocytes, 5% red blood cells), were added to each well, and cultures were incubated at 37° C. After 20–24 hr, 20 µl of each 10× mefloquine working solution (1280, 640, 320, 160, 80, 40, 20, and 10 ng/ml) was added per well, allowing 4 wells for each mefloquine dilution (Hoffman La Roche, Nutley, N.J.). After 20–24 hr, 0.5 µCi $^3$H-hypoxanthine was added to each well, cultures were incubated at 37° C. and cells were harvested as described. After counting, cpm values were averaged for the four samples at each dilution of mefloquine, this average was multiplied by the proportion of parasites present at that oligonucleotide concentration, and values from different experiments were normalized. Normalized values were then averaged between experiments. IC$_{50}$ values are then determined by non-linear regression analysis.

Representative results in mefloquine resistant W2mef and mefloquine sensitive W2 parasites are shown in FIGS. 2–5. Representative results in mefloquine resistant field isolate strains PR145, TM346, TM336, and TM352, and mefloquine sensitive TM335 are shown in FIG. 6

5. Reversal of Resistance to Quinine and Other Structurally Unrelated Compounds

Experiments were conducted in the same manner as described above for mefloquine resistance. Oligonucleotides (either against pfmdr1 or control sequences) were aliquotted into 96 well microtiter plates in a 0.25 µM or 0.5 µM amounts and 200 µl unsynchronized parasites were added to each well. After 20–24 hr, 2-fold serial dilutions of quinine were added, using four wells for each dilution of drug. Parasites were cultured for 24 hours before $^3$H-hypoxanthine was added to each well, and samples were harvested for scintillation counting 24 hours after that. Data were then averaged, normalized and analyzed by non linear regression to determine the IC$_{50}$. Initially, experiments were done using the W2 and W2mef strain of *P. falciparum*, followed by testing of field isolates. The results are shown in FIG. 7.

6. In Vivo Reversal of Drug Resistance

Rodent malarial strains both sensitive and resistant to drugs (Table 3) are maintained by syringe passage in outbred Swiss mice as described by Peters *(Exp. Parasitol.* (1965) 17:89–90) and by Peters et al. (*Ann. Trop. Med. Parasitol.* (1977) 71:419–427). Drug resistant strains are maintained under drug pressure, by injection of infected mice with certain amounts of drug (see Table 3) at least once during each cycle. For mefloquine reversal experiments, animals are freshly inoculated intravenously with 10$^7$ parasitized cells. They are then injected with an antisense oligonucleotide specific for MDR nucleic acid. After 24 hr, the anti-malarial drugs (see Table 3 for examples and dosages) are injected either subcutaneously or intraperitoneally at the same concentration used for maintenance, and parasitemia is then monitored daily by microscopic examination of thin smears.

Parasitemia is expected to be reduced relative to controls in animals infected with mefloquine-resistant strains (Table 4). Resistance to mefloquine is expected to be reversed in the presence of oligonucleotides directed to pfmdr, but not by oligonucleotides directed to other gene targets. Similarly, chloroquine and quinine resistance may well be reversible using the same MDR-specific oligonucleotides.

TABLE 4

| Strain | Resistance Pattern | Maintenance Dose |
| --- | --- | --- |
| N(K173) | Sensitive to all drugs | — |
| RC | Resistant to MFQ, CQ, Hal, Quin | — |
| N1100 | Resistant to MFQ, Hal; sensitive to CQ | — |
| NHAL | Resistant to MFQ, Hal, CQ; sensitive to Quin | — |
| Q | Resistant to MFQ, CQ, Quin | — |
| RC | CQ | 60 mg/kg |
| N1100 | MFQ | 60 mg/kg |
| NHAL | Hal | 30 mg/kg |
| Q | Quin | 600 mg/kg |

MFQ: mefloquine; CQ: chloroquine; Hal: halofantrine; Quin: quinine.

7. In Vivo Inhibition of Malarial Growth

To examine the efficacy of antisense oligonucleotides directed against malaria in vivo, initial experiments were performed using *P. gallinaceum* parasites grown in young chickens. In this experiment, twenty-four day old Rhode Island Red chicks (200–250 g; SPAFAS Inc., Norwich, Conn.) were used in these studies. Three groups of 4–7 animals each were infected on Day 0 with *gallinaceum* parasites (Dr. Dyann Wirth, Harvard School of Public Health, Boston, Mass.) by intravenous injection of 0.2 ml infected blood (approximately $2 \times 10^8$ parasites) via the wing vein. One group was maintained as an infection control, and received no further treatment, while the remaining two groups received daily intravenous injections of oligonucleotides (10 mg/animal suspended in 10 mM Tris, 1 mM EDTA, pH 8.0; approximately 50 mg/kg body weight, or 8 $\mu$M final concentration) starting on the day of infection and for the next 4 days. Oligonucleotides were phosphorothioate-linked 18mers synthesized by standard methods. Two different oligonucleotides were used: "281": (5'-AAA ATA ATT TCT TCG TAG-3' (SEQ ID NO:15)) was an antisense sequence targeted against the dihydrofolate reductase-thymidylate synthase (DHFR) gene from *P. falciparum*. This sequence corresponds to an internal portion of the 27mer designated RB 105 (SEQ ID NO:2) which had previously been shown to be highly inhibitory to *P. falciparum* in vitro culture (Barker et al. (1996) *Proc. Natl. Acad. Sci. USA* 93:514–518). The sequence of the "282" oligonucleotide (5'-CTA CGA AGA AAT TAT TTT-3' (SEQ ID NO:15) is complementary to that of antisense oligonucleotide 281, and served as a "sense" strand control for sequence specificity. After infection, parasitemia was monitored daily by microscopic examination of blood smears strained with DiffQuik™ (Baxter Healthcare Corp., McGraw Park, Ill.) according to the manufacturers' instructions.

In animals which received no antisense oligonucleotides, parasitemia rose rapidly over the next 4 days, achieving an average parasitemia of 78%. At this point, these animals were visibly ill from the infection, and by Day 5, all had died. In contrast, average parasitemia among animals which received daily injections of antisense oligonucleotide 281 reached only 7% by Day 4 post infection, indicating a 91% reduction in infection compared with untreated controls. Among this group, 2/5 animals survived through Day 7, two days after the last injection of antisense oligonucleotide, at which point the experiment was terminated.

These results clearly show that parasitemia is significantly lowered ($P<0.0001$) when infected animals are treated with antisense oligonucleotide directed against DHFR. In contrast, in the remaining group of animals which had received the "sense" strand control oligonucleotide, average parasitemia by Day 4 was intermediate between that of infection controls and antisense oligonucleotide treated animals, reaching 40% by Day 4. This represents an approximately 6-fold increase over parasitemia in animals which received the antisense oligonucleotides. Survival of animals in this group was also intermediate between that of animals in the other two groups: 2 out of 4 animals were dead by Day 5, while the remaining 2 died by Day 6. Thus, treatment of malaria-infected animals with antisense oligodeoxynucleotides can reduce both infection and mortality. These experiments demonstrate that results obtained in vitro are predictive of in vivo results for inhibition of parasites. Based on this correlation, it can be predicted that in vivo models for the reversal of drug resistance will also yield results similar to those described herein using the in vitro model for the reversal of mefloquine and quinine resistance. Thus, these results strongly suggest that antisense therapy would be a useful clinical treatment for treatment of drug-resistant human disease.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic oligonucleotide comprising a nucleotide sequence complementary pfmdr1 nucleic acid, wherein the nucleotide sequence is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

2. The oligonucleotide of claim 1, which is modified, the modification comprising an internucleotide linkage selected from the group consisting of phosphorothioates, phosphorodithioates, alkylphosphonates, alkylphosphonothioates, phosphoramidates, carbamates, acetamidates, carboxymethyl esters, carbonates, and phosphate triesters.

3. The oligonucleotide of claim 2 having at least one phosphorothioate internucleotide linkage.

4. The oligonucleotide of claim 2 having phosphorothioate internucleotide linkages.

5. A method of down-regulating the expression of a pfmdr1 nucleic acid comprising contacting the nucleic acid with a synthetic oligonucleotide comprising a nucleotide sequence complementary to a pfmdr1 nucleic acid, wherein the nucleotide sequence is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

6. The method of claim 5, wherein the oligonucleotide is modified, the modification comprising an internucleotide linkage selected from the group consisting of phosphorothioates, phosphorodithioates, alkylphosphonates, alkylphosphonothioates, phosphoramidates, carbamates, acetamidates, carboxymethyl esters, carbonates, and phosphate triesters.

7. The method of claim 6, wherein the oligonucleotide comprises at least one phosphorothioate internucleotide linkage.

8. The method of claim 6, wherein the oligonucleotide comprises phosphorothioate internucleotide linkages.

9. A method of resensitizing an anti-malarial drug-resistant Plasmodium parasite to an anti-malarial drug, comprising the steps of:
(a) culturing the parasite in the presence of a synthetic oligonucleotide comprising a nucleotide sequence complementary to a pfmdr1 nucleic acid for a time sufficient to enable the oligonucleotide to hybridize to the nucleic acid, wherein the nucleotide sequence is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13; and
(b) contacting and culturing the parasite with an anti-malarial drug in the presence of the oligonucleotide.

10. The method of claim 9, wherein the parasite is contacted and cultured with an anti-malarial drug selected from the group consisting of mefloquine, quinine, chloroquine, and derivatives thereof.

11. The method of claim 10, wherein the parasite is contacted and cultured with mefloquine.

12. The method of claim 10, wherein the parasite is contacted and cultured with quinine.

13. A method of resensitizing a drug-resistant infectious organism to an anti-infectious organism drug, thereby reversing the drug-resistant phenotype of the organism, the method comprising the steps of:

(a) culturing the infectious organism in the presence of a synthetic oligonucleotide comprising a nucleotide sequence complementary to a nucleic acid required for the drug-resistant phenotype for a time sufficient to enable the oligonucleotide to hybridize to the nucleic acid, wherein the nucleotide sequence is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13; and (b) contacting and culturing the parasite with an anti-infectious organism drug in the presence of the oligonucleotide.

14. The method of claim 13, wherein the oligonucleotide is modified, the modification comprising an internucleotide linkage selected from the group consisting of phosphorothioates, phosphorodithioates, alkylphosphonates, alkylphosphonothioates, phosphoramidates, carbamates, acetamidates, carboxymethyl esters, carbonates, and phosphate triesters.

15. The method of claim 14, wherein the oligonucleotide comprises at least one phosphorothioate internucleotide linkage.

16. The method of claim 14, wherein the oligonucleotide has internucleotide linkages.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 1:

TCTTCCTCTC TCTACCCACG CTCTC                                            25

(2) INFORMATION FOR SEQ ID NO: 2:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 2:

TCTTAAAAAT AATTTCTTCG TAGTTAA                                          27

(2) INFORMATION FOR SEQ ID NO: 3:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 3:

TCATATAATT ATTTACTACG TTGTAAA                                          27

(2) INFORMATION FOR SEQ ID NO: 4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 4:

TGTTATATAA AAATTGTTCC TACTTTT                                          27

(2) INFORMATION FOR SEQ ID NO: 5:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 5:

CCATCTTTTT TCTCTTTCTG CTCTTTACC                               29

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 6:

GGTAATGTTC CTCCTGATAA TACAGC                                  26

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 7:

CCTATAGATA CTAATGATAA TATTATAGG                               29

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 8:

CGTACCAATT CCTGAACTCA CTTGTTC                                 27

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 9:

```
GGACTATTTA TAATAATTCT TGTACC                                              26

(2) INFORMATION FOR SEQ ID NO: 10:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 10:

CCCTTCTTTT AGAGTAAAAC TTAAATC                                             27

(2) INFORMATION FOR SEQ ID NO: 11:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 11:

CCATAATATC TCCTTCGGTT GG                                                  22

(2) INFORMATION FOR SEQ ID NO: 12:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 12:

CGAAATTAAA GAAAATTTT TATTTTC                                              27

(2) INFORMATION FOR SEQ ID NO: 13:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 13:

CCTGATAATT TGGATGCATT GCTTCC                                              26
```

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 14:

TTACTACGAA GAAATTATTT TTAAGA      26

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 15:

AAAATAATTT CTTCGTAG      18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 16:

CTACGAAGAA ATTATTTT      18